(12) United States Patent
Hentz et al.

(10) Patent No.: US 10,132,957 B2
(45) Date of Patent: Nov. 20, 2018

(54) OPTOMECHANICAL DEVICE FOR ACTUATING AND/OR DETECTING MOVEMENT OF A MECHANICAL ELEMENT, IN PARTICULAR FOR GRAVIMETRIC DETECTION

(71) Applicant: Commissariat à l'énergie atomique et aux énergies alternatives, Paris (FR)

(72) Inventors: Sébastien Hentz, Varces Allieres et Risset (FR); Laurent Duraffourg, Voiron (FR); Guillaume Jourdan, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 636 days.

(21) Appl. No.: 14/519,390

(22) Filed: Oct. 21, 2014

(65) Prior Publication Data

US 2015/0107357 A1 Apr. 23, 2015

(30) Foreign Application Priority Data

Oct. 22, 2013 (FR) ...................................... 13 60282

(51) Int. Cl.
*G01V 7/00* (2006.01)
*G01D 5/26* (2006.01)
(Continued)

(52) U.S. Cl.
CPC .............. *G01V 7/005* (2013.01); *G01D 5/266* (2013.01); *G01D 5/268* (2013.01);
(Continued)

(58) Field of Classification Search
CPC ................................ G02B 6/10; G02B 6/3536
See application file for complete search history.

(56) References Cited

U.S. PATENT DOCUMENTS 4,204,742 A * 5/1980 Johnson ............... G02B 6/3576
356/43
5,162,691 A * 11/1992 Mariani ................. H03H 9/172
310/321

(Continued)

FOREIGN PATENT DOCUMENTS

WO 2012/034949 A1 3/2012
WO 2012/034951 A1 3/2012

(Continued)

OTHER PUBLICATIONS

I. Bargatin et al.,"Large-Scale Integration of Nanoelectromechanical Systems for Gas Sensing Applications" Nano Letters.

(Continued)

*Primary Examiner* — Hezron E Williams
*Assistant Examiner* — Tran M Tran
(74) *Attorney, Agent, or Firm* — Pearne & Gordon LLP (57) ABSTRACT

Optomechanical device for actuating and/or detecting movement of a mechanical element, in particular for gravimetric detection. It includes a support with a mechanical element anchored to the support which is designed to move relative to the element, and a device for actuating and/or detecting movement or of variations in frequency of movement of the element. A portion of the device is arranged beneath at least part of the element, between the element and the support. The device includes a fixed optical device with at least one optical waveguide arranged beneath all or part of the element at a determined distance from the element, and which is designed to propagate at least one optical wave having a given wavelength designed to interact with the element. The optical waveguide is at a determined distance from the mechanical element so that the evanescent field of the optical waveguide interacts with the mechanical element.

14 Claims, 9 Drawing Sheets

(51) Int. Cl.
*G01D 5/353* (2006.01)
*G02B 6/35* (2006.01)
*G01N 5/00* (2006.01)
*G02B 6/12* (2006.01)
*G01G 3/16* (2006.01)
*G01N 15/06* (2006.01)
*G02B 6/293* (2006.01)

(52) U.S. Cl.
CPC ........... *G01D 5/35312* (2013.01); *G01G 3/16* (2013.01); *G01N 5/00* (2013.01); *G01N 15/0606* (2013.01); *G02B 6/12007* (2013.01); *G02B 6/29338* (2013.01); *G02B 6/3536* (2013.01)

(56) References Cited

U.S. PATENT DOCUMENTS

| | | | | |
|---|---|---|---|---|
| 5,787,212 | A * | 7/1998 | Hong | B82Y 35/00 250/227.27 |
| 6,304,697 | B1 * | 10/2001 | Toyohara | G02F 1/3132 385/30 |
| 6,385,363 | B1 * | 5/2002 | Rajic | G02B 6/3502 385/16 |
| 6,392,233 | B1 * | 5/2002 | Channin | G01J 5/40 250/234 |
| 6,411,752 | B1 * | 6/2002 | Little | G02B 6/12002 385/17 |
| 6,668,111 | B2 * | 12/2003 | Tapalian | G01P 15/093 385/27 |
| 6,909,824 | B1 | 6/2005 | Messica | |
| 6,970,619 | B2 * | 11/2005 | Baumann | G02B 6/12007 372/92 |
| 7,031,563 | B2 * | 4/2006 | Block | G02B 6/12007 385/15 |
| 7,120,332 | B1 * | 10/2006 | Spoonhower | G02B 6/29343 385/25 |
| 7,285,736 | B2 * | 10/2007 | Korpi | G01G 3/13 177/210 FP |
| 7,310,459 | B1 * | 12/2007 | Rahman | G02B 6/12007 385/14 |
| 7,336,859 | B2 * | 2/2008 | Sanders | B82Y 20/00 385/12 |
| 7,474,810 | B2 * | 1/2009 | Bratkovski | G02B 6/107 385/1 |
| 7,532,790 | B2 * | 5/2009 | Smith | G02B 6/12007 385/129 |
| 7,583,874 | B2 * | 9/2009 | Rakich | B82Y 20/00 359/346 |
| 7,622,705 | B2 * | 11/2009 | Fan | G01N 21/6428 250/216 |
| 8,009,937 | B2 * | 8/2011 | Mathai | G02B 6/12007 257/431 |
| 8,009,943 | B2 * | 8/2011 | Bratkovski | G02F 1/095 385/16 |
| 8,059,922 | B2 * | 11/2011 | Fattal | B82Y 20/00 385/2 |
| 8,115,937 | B2 * | 2/2012 | Needham | G01J 5/38 356/450 |
| 8,179,935 | B2 * | 5/2012 | Santori | G02B 6/12007 359/346 |
| 8,270,781 | B2 * | 9/2012 | Lo | B01L 3/502707 385/12 |
| 8,280,214 | B2 * | 10/2012 | Yang | G01N 21/05 385/12 |
| 8,483,522 | B2 * | 7/2013 | Heidrich | G02B 6/3508 385/14 |
| 8,493,562 | B2 * | 7/2013 | Kopp | G02B 6/12002 356/364 |
| 8,542,365 | B2 * | 9/2013 | Pruessner | G01G 3/165 356/480 |
| 8,542,960 | B2 * | 9/2013 | Fattal | G02B 6/12007 385/14 |
| 8,676,002 | B2 * | 3/2014 | Grenouillet | G02B 6/13 257/E33.023 |
| 8,717,569 | B2 * | 5/2014 | Lo | B01L 3/502707 356/436 |
| 8,925,385 | B2 * | 1/2015 | Korpi | G01G 3/16 73/19.03 |
| 8,947,176 | B2 * | 2/2015 | Hentz | H03H 9/02338 257/415 |
| 9,008,467 | B2 * | 4/2015 | Quitoriano | G02F 1/025 385/2 |
| 9,069,004 | B2 * | 6/2015 | Bhave | G01P 15/093 |
| 9,134,221 | B2 * | 9/2015 | Lo | G01N 15/1459 |
| 9,293,686 | B2 * | 3/2016 | Hentz | H03H 9/02259 |
| 9,325,291 | B2 * | 4/2016 | Hentz | H03H 9/02259 |
| 9,331,606 | B2 * | 5/2016 | Hentz | H03H 9/02259 |
| 9,395,177 | B2 * | 7/2016 | Pruessner | G01B 11/14 |
| 9,470,576 | B2 * | 10/2016 | Colinet | G01D 5/02 |
| 9,506,852 | B2 * | 11/2016 | Hentz | G01N 29/022 |
| 9,645,010 | B2 * | 5/2017 | Lo | G01J 3/46 |
| 9,759,552 | B2 * | 9/2017 | Pruessner | G01B 11/14 |
| 9,891,382 | B2 * | 2/2018 | Duraffourg | G01D 5/35312 |
| 9,958,608 | B2 * | 5/2018 | Qi | G02B 6/12007 |
| 2002/0039467 | A1 * | 4/2002 | Amantea | G02B 6/12002 385/16 |
| 2006/0222292 | A1 | 10/2006 | Spoonhower | |
| 2009/0199638 | A1 * | 8/2009 | Jeffs | G01D 5/243 73/579 |
| 2010/0265504 | A1 | 10/2010 | Kopp | |
| 2011/0255822 | A1 * | 10/2011 | Zheng | G02B 6/3508 385/14 |
| 2011/0305413 | A1 * | 12/2011 | Heidrich | G02B 6/3508 385/2 |
| 2012/0063717 | A1 | 3/2012 | Grenouillet | |
| 2013/0154440 | A1 | 6/2013 | Hentz | |
| 2013/0160550 | A1 | 6/2013 | Hentz | |
| 2013/0214644 | A1 | 8/2013 | Hentz | |
| 2014/0013848 | A1 | 1/2014 | Colinet | |
| 2014/0250980 | A1 | 9/2014 | Hentz | |
| 2015/0107357 | A1 * | 4/2015 | Hentz | G01D 5/266 73/382 G |

FOREIGN PATENT DOCUMENTS

WO 2012/034990 A1 3/2012
WO 2012/172204 A1 12/2012

OTHER PUBLICATIONS

Search Report issued in French Patent Application No. FR 13 60282 dated Aug. 1, 2014.
J. Chaste et al.,"A nonomechanical mass sensor with yoctogram resolution" Nature Nanotechnology, Apr. 1, 2012.
S. Dohn et al., "Mass and position determination of attached particles on cantilever based mass sensors" Review of Scientific Instruments, vol. 78, 2007.
K.L. Ekinci et al., "Ultimate limits to inertial mass sensing based upon nanoelectromechanical systems" Journal of Applied Physics, vol. 95, No. 5, Mar. 1, 2004.
T.J. Kippenberg et al., "Cavity Optomechanics:Back-Action at the Mesoscale" Science, vol. 321, Aug. 29, 2008.
S. Guillon et al., "Biological functionalization of massively parallel arrays of nanocantilevers using microcontact printing" Sensors and Actuators B: Chemical, vol. 161, 2012.
P Ivaldi et al., "50nm think AlN film-based piezoelectric cantilevers for gravimetric detection" Journal of Micromechanics and Microengineering, vol. 21, 2011.
Lasse J. Kauppinen et al., "Micromechanically tuned ring resonator in silicon on insulator" Optics Letters, vol. 36, No. 7, Apr. 1, 2011.
G. Anetsberger et al., "Near-field cavity optomechanics with nanomechanical oscillators" Nature Physics, vol. 5, Dec. 2009.
Gino Putrino et al., "Integrated Resonant Optical Readout Applicable to Large Arrays of MEMS Beams" IEEE Photonics Technology Letters, vol. 24, No. 24, Dec. 15, 2012.
Mo Li et al., "Ultra-senstivie NEMS-based cantilevers for sensing, scanned probe and very high-frequency application" Nature Nanotechnology, 2007.

(56) References Cited

OTHER PUBLICATIONS

E. Mile et al., "In-plane nanoelectromechanical resonators based on silicon nanowire piezoresistive detection" Nanotechnology, vol. 21, 2010.
A.K. Naik et al., "Towards single-molecule nanomechanical mass spectrometry" Nature Nanotechnology, Jun. 21, 2009.
R. Rekha et al., "Design of MOEM Vibration Sensor Using Optical MicroRing Resonator and MicroCantilever Beam" Tencon, 2011.
Houxun Miao et al., "A MEMS Controlled Cavity Optomechancial Sensing System" Lasers and Electro-optics, May 6, 2012.
U.S. Appl. No. 14/519,353, filed Oct. 21, 2014.
Mo Li et al., "Broadband all-photonic transduction of nanocantilevers" Nature Nanotechnology, 2009.
Mani Hossein-Zadeh et al., "An Optomechanical Oscillator on a Silicon Chip" IEEE Journal of Selected Topics in Quantum Electronics, vol. 16., No. 1, Jan./Feb. 2010.
M.S. Hanay et al. "Single-protein nanomechanical mass spectrometry in real time" Nature Nanotechnology, vol. 7, Sep. 2012.
Search Report issued in Application No. EP 14 18 9702 dated Mar. 10, 2015.
S. V. Pham et al., "Read-Out of Cantilever Bending With a Grated Waveguide Optical Cavity" IEEE Photonics Technology Letters, vol. 23, No. 4, Feb. 15, 2011.

\* cited by examiner

OPTOMECHANICAL DEVICE FOR ACTUATING AND/OR DETECTING MOVEMENT OF A MECHANICAL ELEMENT, IN PARTICULAR FOR GRAVIMETRIC DETECTION

TECHNICAL FIELD

The invention relates to an optomechanical device for actuating and/or detecting movement of a mechanical element.

The latter may be a resonating device, in which case the mechanical element constitutes a resonator, or a non-resonating device.

The invention applies in particular to gravimetric detection, preferably large capture surface gravimetric detection.

It also applies to any type of frequency-based detection, for example in the field of terahertz imaging or of bolometry.

STATE OF THE PRIOR ART

In-plane actuated resonant devices are already known. All these devices comprise beams which are parallel to the substrates of these devices. Reference should be made to the following documents:

WO 2012/034949, invention by S. Hentz
WO 2012/034951, invention by S. Hentz et al.
WO 2012/034990, invention by S. Hentz.

The principles of resonant mass detection will now be summarised.

Consider a particle or a set of particles of total mass $m_p$, landing on the surface of a resonator of stiffness k and of effective mass m. The resonance frequency of the resonator then becomes equal to:

$$f = \frac{1}{2\pi}\sqrt{\frac{k}{m+m_p}}.$$

The frequency response peaks (open loop), before and after deposition of the mass $m_p$, are therefore shifted by an amount Δf which to a good approximation is $$-\frac{m_p}{2m} \cdot \frac{1}{2\pi}\sqrt{\frac{k}{m}}.$$

When the resonator is in closed loop mode, then the resonance frequency can be monitored in real time using means of electrical transduction and means for closing the loop.

It can be seen that the adsorption of an individual particle or of a group of particles of an analyte on the surface of the resonator causes a sudden decrease in the latter's resonance frequency. The mass of the particle or of the group of particles can then be deduced from the measurement of the sudden change in frequency Δf.

The detection principle that has just been described is entirely generic in nature, and various devices are known for applying it, in particular surface acoustic wave resonators, bulk acoustic wave resonators, quartz crystal microbalances and Micro-Electro-Mechanical System (MEMS) beams.

The resonant device may however advantageously be a Nano-Electro-Mechanical System (NEMS) since the expression for the frequency shift, Δf, given above, shows that the smaller the total mass of the resonator is, then the more sensitive is the frequency to an addition of mass. Resonant devices with nanometric dimensions therefore have a certain advantage not only in terms of sensitivity but also in terms of detection limits. Thus, using NEMS, masses that are $10^{12}$ times smaller than those that have been measured with quartz crystal microbalances can be measured. On this matter, reference should be made to the following document:

K. L. Ekinci, Y. T. Tang and M. L. Roukes, 2004, "Ultimate limits to inertial mass sensing based upon nano-electromechanical systems", *Journal of Applied Physics* 95 (5): 2682. doi:10.1063/1.1642738.

Likewise, a mass of the order of 1 yg ($10^{-27}$ kg) has recently been measured. On this matter, reference should be made to the following document:

J. Chaste, A. Eichler, J. Moser, G. Ceballos, R. Rurali and A. Bachtold, 2012, "A nanomechanical mass sensor with yoctogram resolution", *Nature Nanotechnology* 7: 301-304. doi:10.1038/nnano.2012.42.

There are many applications for resonant mass detection. The following examples could be cited (1): chemical sensors for gas detection, (2) biological sensors in liquid environments for detection of biological cells and (3) NEMS-MS; that is, NEMS-based mass spectrometry. For these applications the detection limit (the lowest detectable mass) is naturally of prime importance, not only in order to determine the amount of material measured as precisely as possible, but also to detect species that are highly dispersed or diluted in large volumes of a carrier element.

(1) In the case of chemical sensors for gas detection, a NEMS is used whose surface may be covered with a functionalisation layer which has a specific chemical affinity towards certain species to be measured. The particles which correspond to these species are absorbed into this layer or onto the entire surface of the NEMS in a homogeneous manner.

When the concentration to be measured becomes very low, the probability of species being captured by the very small surface area of the NEMS becomes very small. Recourse may then be made to the use of arrays which are collectively addressed in order to make best use of the very high sensitivity of the resonators. A large capture surface may, however, also be used. On this matter, reference should be made to the following document:

I. Bargatin, E. B. Myers, J. S. Aldridge, C. Marcoux, P. Brianceau, L. Duraffourg, E. Colinet, S. Hentz, P. Andreucci, and M. L. Roukes, 2012, "Large-scale integration of nano-electromechanical systems for gas sensing applications", *Nano letters* 12 (3) (14 March): 1269-304. doi:10.1021/nnano.2012.42.

and more specifically to FIG. 1 of this document.

(2) In the case of biological sensors in a liquid environment the set of problems is the same as for chemical sensors, but is even more acute: the resonant device is then placed in the liquid environment wherein the biological particles to be detected are to be found. They may have to be detected individually when they are at low concentrations. Similarly, there may be a need to use arrays of resonators, individually addressed or not, functionalised or otherwise. On this matter, reference should be made to the following document:

S. Guillon, S. Salomon, F. Seichepine, D. Dezest, F. Mathieu, A. Bouchier, L. Mazenq, C. Thibault, C. Vieu, T. Leïchlé and L. Nicu, 2012, "Biological functionalization of massively parallel arrays of nanocantilevers using micro-contact printing", *Sensors and Actuators B: Chemical* 161 (January): 1135-1138. doi:10.1016/j.snb.2011.10.084 and more specifically to FIG. 1 of this document.

(3) In the case of NEMS-MS, this involves measuring the mass of each particle (for example a biological particle) of a mixture which is initially in the liquid phase and which it is wished to project onto an NEMS under vacuum, in order to obtain the mass spectrum of the content of the mixture, for example in biomedical identification applications. Such a system is shown in FIG. 1 of the following document to which reference should be made:

A. K. Naik, M.S. Hanay, W. K. Hiebert, X. L. Feng and M. L. Roukes, 2009, "Towards single-molecule nanomechanical mass spectrometry", *Nature Nanotechnology* 4: 445-450. doi:10.1038/NNANO.2009.152.

A major problem with this system is the use of a single NEMS to detect the particles which are projected onto its surface: the latter may typically be 1 $\mu m^2$ whereas, depending on the injection system, the particle beam may have a projected area of the order of between a few square nanometers and a few square centimeters.

This again shows the critical aspect of using extremely dense arrays of NEMS in order to maximise the capture surface. In the case of NEMS-MS, however, an additional problem arises when compared with the two previous cases: this relates to the measurement of the mass of a particle which is a point mass, or at least smaller that the surface area of the resonator and which is not spread over this surface area. The frequency shift induced by the addition of a particle depends not only on the mass but also on the position at which the particle arrives on the resonator. It is then necessary to measure several resonance frequencies, and not a single one, in real time. On this matter, reference should be made to the following document:

S. Dohn, W. Svendsen, A. Boisen and O. Hansen, 2007, "Mass and position determination of attached particles on cantilever based mass sensors", *Review of Scientific Instruments* 78: 103303. doi:10.1063/1.2804074.

The mechanical structure does not necessarily have to be resonant, as in the case of where it is desired to measure the forces exerted by an external biological object, particle or molecule on a mechanical structure.

In each of the cases (1) to (3), the (thee-dimensional) elements such as beams or cantilevers used for detecting particles have one dimension (length) which is at least 10 times greater than the other two dimensions (and may therefore be regarded as being one-dimensional). This dimension is in the plane of the substrate whereon the device under consideration is formed.

Furthermore, the means of transduction used are (a) either in the same plane as the device, or (b) in a plane parallel to that of the device and separated from the latter by layers deposited on the device itself.

On the matter of case (a), reference should be made to the following document:

E. Mile, G. Jourdan, I. Bargatin, S. Labarthe, C. Marcoux, P. Andreucci, S. Hentz, C. Kharrat, E. Colinet and L. Duraffourg, 2010, "In-plane nanoelectromechanical resonators based on silicon nanowire piezoresistive detection", *Nanotechnology* 21 (16) (23 April): 165504. doi:10.1088/0957-4484/21/16/165504 and in particular to FIG. 1 of this document.

On the matter of case (b), reference should be made to the following document:

Mo Li, H. X. Tang and M. L. Roukes, 2007, "Ultrasensitive NEMS-based cantilevers for sensing, scanned probe and very high-frequency applications", Nature nanotechnology 2 (2) (February): 114-20. doi:10.1038/nnano.2006.208 and in particular to FIG. 1 of this document. Reference should also be made to the following document:

P. Ivaldi, J. Abergel, M. H. Matheny, L. G. Villanueva, R. B. Karabalin, M. L. Roukes, P. Andreucci, S. Hentz and E. Defaÿ, 2011, "50 nm thick AlN film-based piezoelectric cantilevers for gravimetric detection", *Journal of Micromechanics and Microengineering* 21: 085023. doi:10.1088/0960-1317/21/8/085023 and in particular to FIG. 3 of this document.

Connections must therefore emerge in the same plane as the device itself.

These characteristics (one-dimensional elements in the plane of the substrate, the need for the connections to emerge in the plane of the device) prevent good SA/SI ratios from being achieved, where SA represents the active surface area, that is, the vibrating area of the MEMS or of the MEMS under consideration, and SI represents the inactive surface area, that is, the surface area which does not vibrate. Thus the surface area for capture of the elements to be detected is extremely small. It is for example very difficult to achieve an active surface density which is greater than 1% with these characteristics.

DESCRIPTION OF THE INVENTION

The aim of the present invention is to overcome the above drawbacks.

According to one aspect of the invention, the surface of a wafer is cut up into elementary "pixels" which have a high coverage density, and everything which does not play a part in this capture surface (for example means of transduction, connections, contacts) is placed beneath these pixels.

It should be stated that the invention is not restricted to the use of a wafer: the support that the device disclosed by the invention comprises may be obtained in other ways.

According to another aspect of the invention, optical transduction is used. Such transduction is simpler than an electrical transduction system, for example a piezoresistive system, which requires that contacts of very small size be made, with a high density, at levels below the active surface, by means of interconnections of the sort that are used in CMOS methods. In practice this can even lead to CMOS co-integration being required, since there may be a very large number of electrical connections.

Specifically, this invention discloses an optomechanical device comprising:
  a support, and on this:
  at least one mechanical element which is anchored to the support and which is designed to move relative to the latter, and
  a device for actuating the mechanical element and/or for detecting movement of the mechanical element or of variation in the frequency of movement, where at least a portion of the actuation device and/or detection device is arranged beneath all or part of the mechanical element, between the latter and the support,
  the optomechanical device being characterised in that the actuation device and/or detection device comprises an optical device which is fixed with respect to the support, which comprises at least one optical waveguide, which is arranged beneath all or part of the mechanical element, at a determined distance from the latter, and which is designed to propagate at least one optical wave which has a given wavelength, designed to interact with the mechanical element, and in that the optical waveguide is at a determined distance from the mechanical element so that the evanescent field of the optical waveguide interacts with the mechanical element.

By "evanescent field interacting with the mechanical element" we mean that this evanescent field is perturbed by the displacement of the mechanical element.

The mechanical element or elements may be resonant or non-resonant.

The support may have a flat surface. The mechanical element may also have an elongated shape, for example in the form of a beam, which may or may not be perpendicular to this surface.

Preferably, the mechanical element has either an element which is perpendicular to the plane of the layers from which the device is made, having an end anchored to the support and an end able to move in a plane parallel to the plane of the layers, or an element parallel to the plane of the layers, suspended to the support via at least two ends, and able to move perpendicular to the plane of the layers.

According to one specific embodiment, said mechanical element forms a mechanical resonator with a given resonance frequency.

The number of optical devices may be less than or equal to the number of mechanical elements.

In the case of the above mentioned specific embodiment, the device disclosed by the invention may comprise one optical device per mechanical element or one optical device for a group of mechanical elements with resonance frequencies which differ from each other.

According to one specific embodiment of the optomechanical device disclosed by the invention, the optical device moreover comprises an optical resonator which is optically coupled to the waveguide. This optical resonator may be in the form of a ring. The invention is not restricted to this shape however: other shapes can also be envisaged, such as a 'racetrack' shape, an oval shape etc. or a combination of these shapes.

According to one specific embodiment of the invention, the mechanical element comprises a receiving zone designed to receive one or more particles which can cause or modify the movement of the mechanical element for the purpose of determining a physical property of the particle or of the particles from a signal supplied by the detection device.

The mechanical element may comprise a substantially rectilinear beam which has a first end anchored to the support, and a second end provided with a plate which forms the receiving zone.

In this case, according to one specific embodiment of the invention, the beam is substantially perpendicular to the support and the plate is substantially perpendicular to the beam.

According to one specific embodiment of the optomechanical device disclosed by the invention, the mechanical element forms a mechanical resonator whose resonance frequency varies when the receiving zone receives the particle or particles.

According to a first specific embodiment of the invention, the receiving zone is designed to receive material particles.

The term "material particle" is used to refer to an atom or an aggregate of atoms, a molecule, an aggregate of molecules or even a group of elements (in particular of cells or proteins) linked by non-covalent bonds.

According to a second specific embodiment, the receiving zone comprises a material designed to absorb particles made up of photons in a predefined range of electromagnetic frequencies.

BRIEF DESCRIPTION OF THE ILLUSTRATIONS

The present invention will be better understood on reading the embodiment examples given hereafter, which are given for purely informative purposes and which are not in any way restrictive, whilst referring to the appended drawings in which.

DETAILED DESCRIPTION OF SPECIFIC EMBODIMENTS

Figure 1:
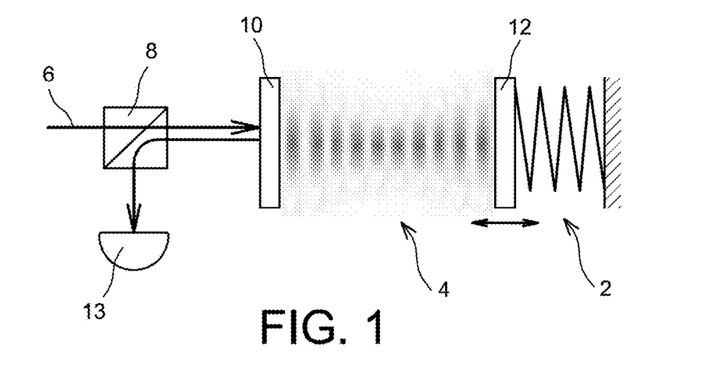
FIG. 1 schematically shows the principle of optomechanical detection.

According to one aspect of the invention, near-field optical transduction is used rather than electrical transduction. The principle of this transduction process is schematically shown in FIG. 1.

On this matter, reference should be made to the following document:

T. J. Kippenberg et al., 2008, Cavity optomechanics: back-action at the mesoscale, Science (New York, N.Y.), 321(5893), pp. 1172-6.

The transduction process is based on the coupling of a mechanical degree of freedom (mechanical oscillator 2) with an optical degree of freedom which is the result, for example, of an electromagnetic field created in an optical cavity 4. As can be seen, the latter is supplied by a laser beam 6, through a semi-transparent mirror 8 and is demarcated by another semi-transparent mirror 10 and by a moving mirror 12 which forms part of the mechanical oscillator. In practice the above-mentioned coupling is achieved when a displacement of moving mirror 12 modifies the resonance modes of the cavity 4.

Reference 13 designates a photodetector of phase/amplitude of the light coming from the semi-transparent mirror 10.

Moreover the evanescent field of an optical waveguide is sensitive to changes in the surrounding medium (for example, refractive index, the presence or otherwise of an object, variation of distance relative to the latter) which consequently has an effect on the propagation modes of the electromagnetic field.

In a resonant cavity of the micro-disk type which has high finesse values, this may lead to significant displacement of the optical resonance frequency. An object coupled to a resonant cavity by the evanescent field of the optical waveguide may modulate the optical resonance frequency of the cavity at the latter's mechanical vibration frequency.

Figure 2:
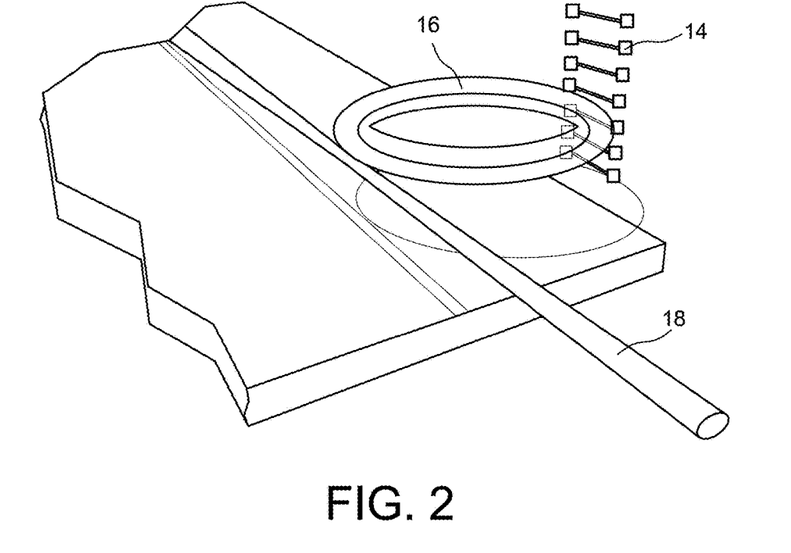
FIG. 2 schematically show the coupling of a NEMS with a resonant optical ring.

This transduction has already been used at the nanometric scale, as shown in FIG. 2, coupling nanometric mechanical devices 14 with ring-shaped optical resonators, of the resonance type 16, coupled to an optical wave guide 18.

On this matter, reference should be made to the following document:

G. Anetsberger et al., 2009, Near-field cavity optomechanics with nanomechanical oscillators, *Nature Physics,* 5(12), pp. 909-914.

This has enabled displacement resolutions of less than 1 fm/Hz$^{1/2}$ to be achieved. Such transduction also allows actuation to occur as a result of optical gradient forces and therefore allows fully-optical transduction of the mechanical resonator. On this matter, reference should be made to the following document:

M. Li et al., 2009,Broadband all-photonic transduction of nanocantilevers, *Nature Nanotechnology,* 4 (June), pp. 377-382.

In addition to excellent mechanical displacement measurement resolution, to a wide dynamic range and the possibility of fully-optical operation, this type of transduction possesses many other advantages.

For example, under certain condition (strong coupling, comparable optical and mechanical time constants), back-action effects can be obtained which result in auto-oscillation. This greatly simplifies the control and servo-operation of the mechanical device at its resonance frequency, or enables noise to be reduced. On this matter, reference should be made to the following document:

M. Hossein-zadeh et al., 2010, An Optomechanical Oscillator on a Silicon Chip, *IEEE Journal of selected topics in quantum electronics,* 16(1), pp. 276-287.

Moreover, any type of material can be used, not only conductive materials.

The optical bandwidth is also very large, which means that mechanical devices of very low mass can be used, which resonate at very high frequencies (typically a few gigahertz). This remains practically unachievable with electrical transduction. This bandwidth also makes it possible to multiplex a large number of mechanical devices.

This invention proposes making use of these advantages. According to one aspect of the invention, all or part of the means of optical transduction are placed beneath the mechanical active surface, comprising in particular the mechanical element or elements and the actuation/detection device or devices, where these devices correspond to the optical device 21 in FIGS. 3A and 3B.

Figure 3A:
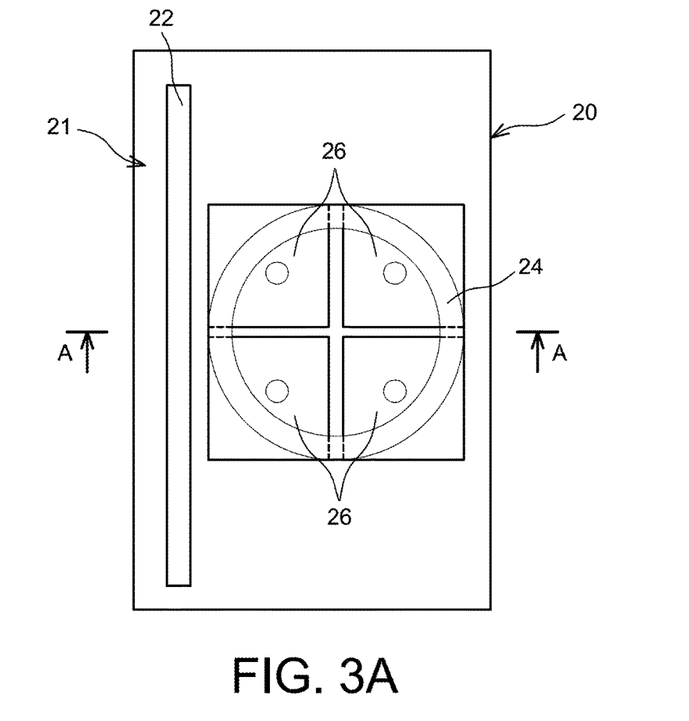
FIGS. 3A and 3B schematically show a specific embodiment of the device disclosed by the invention, FIGS. 4A and 4B schematically show another specific embodiment of the device disclosed by the invention, FIGS. 5A to 5J schematically show the steps of a method for manufacturing a device according to the invention, and FIGS. 6A to 6E schematically show the steps of another method for manufacturing a device according to the invention.
Figure 3B:
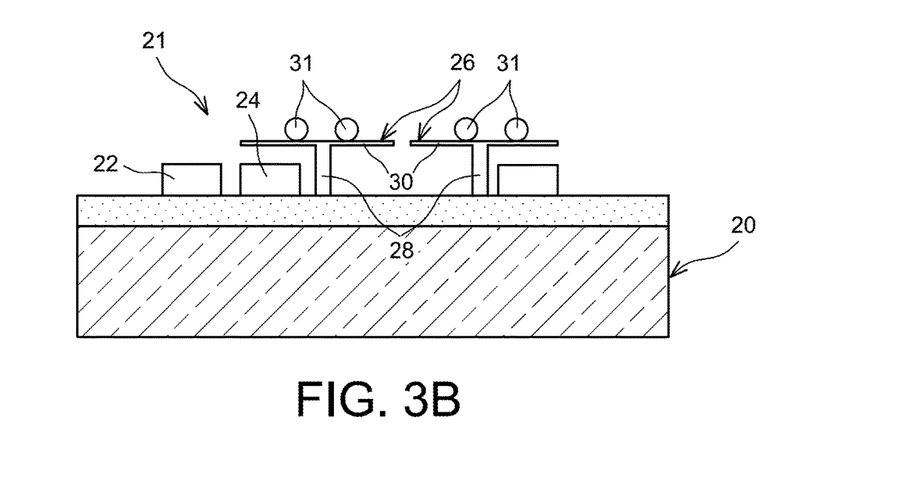

FIGS. 3A and 3B schematically show an example of the optomechanical device disclosed by the invention. FIG. 3A is a top view of the device and FIG. 3B is a section AA through FIG. 3A. In this example the device constitutes an elementary pixel.

It comprises a support 20, and on this an optical device 21 fixed with respect to the support and comprising an optical waveguide 22 (there would be several of these for multi-port operation) and a ring-shaped resonator 24 which is coupled to the waveguide 22 by evanescent coupling and which is tuned, for example, to an optical wavelength close to 1550 nm.

It should be pointed out that the device shown in FIGS. 3A and 3B is supplied with light energy by a laser which is not shown, optically coupled to the waveguide 22.

A certain number of mechanical elements 26 are anchored to the support 20 and are designed to move relative to the latter. These form mechanical resonators. In the example there are four resonators 26 but there may be a single one and these could number up to several tens.

The resonators 26 have resonance frequencies which are close to but different from one another. Each therefore modulates the light energy at its own frequency. The information on each of these frequencies can therefore be recovered by demodulating an optical output signal coming from means of photodetection which are not shown, optically coupled to the optical waveguide.

This frequency-based addressing is similar to the technique disclosed by the following document to which reference should be made:

WO 2012/172204, Système de mesure à résonateurs électromécaniques, procédé de fabrication d'un tel système et procédé de lecture d'au moins deux résonateurs électromécaniques, invention by E. Colinet et al.

Returning to FIGS. 3A and 3B, it can be seen that each mechanical element 26 comprises a substantially rectilinear beam 28, designed to move relative to the support 20. One end of the beam 28 is anchored to the support 20 and the other end is fitted with a substantially flat plate 30, which is perpendicular to the beam and which forms a zone for receiving the particles 31 where it is desired to detect and measure a physical property of these particles. These particles modify the respective resonance frequencies of the beams.

As can be seen, the beams are surrounded by the ring-shaped optical resonator 24 and the latter is beneath the plates 26.

Each of these mechanical elements can vibrate in its fundamental mode (for a sufficiently rigid plate 30, this would be a bending mode of the vertical beam 28), or in one of the higher modes which may be bending modes of the vertical beam 28 (in-plane mechanical movement), or in an extension mode (vibration of the vertical pillar along its axis, with the plate 30 remaining rigid), or again in a bending resonance mode of the plate 30 alone (vertical mechanical movement).

In all cases the beam 28 and the plate 30 must be sufficiently close to the optical resonator 24, typically a few hundred nm from the latter, in order to allow good optomechanical coupling with the optical resonator.

In the case where the addition of mass due to the reception of particles 31 (which modifies the movement of the beams) is distributed homogeneously over the plate (for example gas detection), a single mode per mechanical element allows the added mass to be measured.

In the case of an addition of point mass (detection of a cell or of a single protein for example) in the first three cases of operation single mode can be used to measure the added mass, unlike the situation with conventional NEMS beams or that of the fourth instance of envisaged operation (mode in which the plate 30 undergoes bending vibration) since then the frequency shift also depends on the position of the particle that is to be measured.

On the subject of the case of conventional NEMS beams and of the number of modes required to quantify an addition of point mass, reference should be made to the following document:

M. S. Hanay et al., 2012, Single-protein nanomechanical mass spectrometry in real time, *Nature Nanotechnology,* 7 (September), pp. 602-608.

The use of an arrangement of the type which is shown by FIGS. 3A and 3B, but without an optical resonator, may also be envisaged. In this case the mechanical resonators 26 must be placed along the waveguide 22. The mechanical resonators 26 do not then modulate an optical resonance frequency: they modulate the light energy which is transmitted by the waveguide 22. The respective resonance frequencies of the mechanical resonators 26 must again differ from one another.

On the other hand, in the case where the mechanical structures are not resonant, they modify the transmitted light energy or the frequency of the optical resonators, this change being measured in order to establish the static or quasi-static displacement of the mechanical structures.

An optomechanical device, of the same type as that shown in FIGS. 3A and 3B, allows mechanical resonators to be used which are extremely light and therefore very sensitive to an added mass, leading to a high frequency resonance. In addition the use of a pixel of the sort that is shown in FIGS. 3A and 3B immediately allows a reduction in the number of ports required to address the various mechanical resonators.

Furthermore, a device of the sort that is shown in these FIGS. 3A and 3B allows such pixels to be mounted as a cascade, along a single waveguide and allows extremely dense arrays to be made comprising a large number of mechanical resonators, with the assembly having a minimum number of inputs/outputs. This drastically reduces the inter-connection requirements. In this case the optical resonators are respectively tuned to wavelengths which differ slightly from each other, allowing each of these resonators to be addressed by a specific optical wavelength. All these signals are sent in the same waveguide and demodulated simultaneously at the output of this waveguide.

It is possible to use only a single mechanical resonator covering the entire optical resonator and which comprises, for example, a membrane for this purpose. A minimum diameter (typically 10 µm) is then required for the optical resonator however, so as to ensure an adequate resonance quality. The resulting mechanical device is of large dimensions, which reduces the sensitivity to added mass, unless the device is ultra-thin and slender.

Figure 4A:
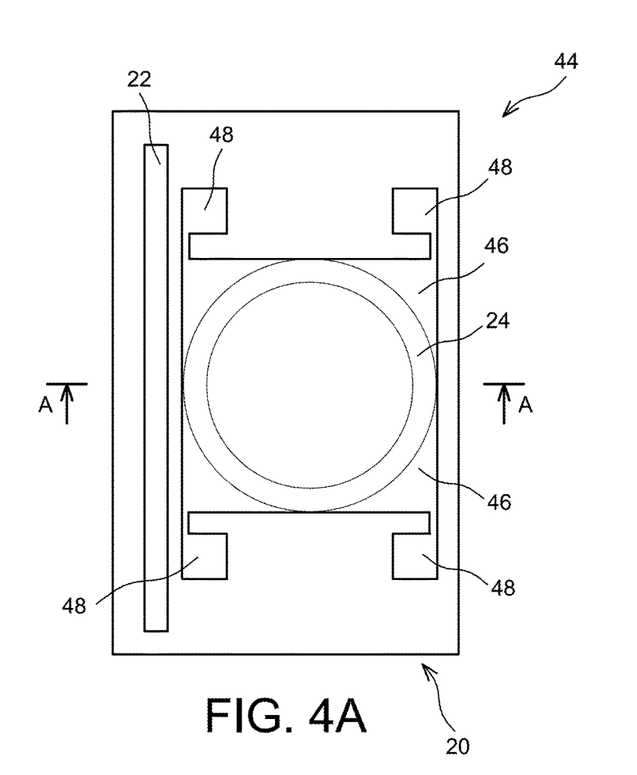
Figure 4B:
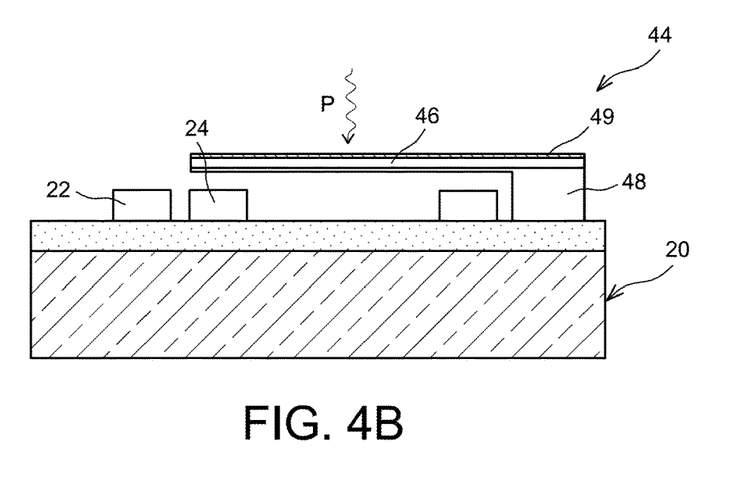

FIGS. 4A and 4B schematically show an example of a pixel comprising a single mechanical resonator for an optical resonator. FIG. 4A is a top view of the pixel and FIG. 4B is a section AA through FIG. 4A.

Once again the support 20 bearing the optical waveguide 22 and ring-shaped optical resonator 24 can be seen. An element 44, forming a mechanical resonator, is associated with the optical resonator 24 and comprises a membrane 46 which covers the entire resonator 24 and which rests on the support 20 by means of pillars 48. In the example shown, the membrane substantially has the form of a square and the pillars are respectively located at the four corners of this square, as can be seen in FIG. 4A.

In the above examples, for the sake of simplicity it has been implicitly assumed that the actuation of each mechanical element and the detection of the variation in the displacement frequency of this element were both optical systems.

The actuation may however also be external and achieved, for example, by means of a vibrating piezoelectric element (or piezoshaker), or be of an electric type, for example electrostatic (by placing an electrode close to the mechanical resonator, for example in a doped zone in a substrate making up the support 20), or be achieved using a conductive electrode, created at the same location as the mechanical resonator.

Moreover, the examples of the invention given above relate to gravimetric detection. The invention, however, is not restricted to one such application: it can also be applied to any type of frequency-based (or static displacement) detection, for example in the field of terahertz imagery or of bolometry.

In this case the plates 30 of FIGS. 3A and 3B and the membrane 46 of FIGS. 4A and 4B may be covered with or even made of a single piece of a material 49 (FIG. 4B) which absorbs photons P in the range of electromagnetic frequencies being studied. In the case of infra-red radiation for bolometry, for example, this material may be titanium.

The manufacture of devices which are in accordance with the invention are considered below.

The waveguides may be made of silicon or of silicon nitride on a rigid support, for example a plate of silicon. It is also possible to make the photonic circuit on a flexible substrate, with optical waveguides made of polymer.

The MEMS or the NEMS likely to be used in the invention may be made of silicon, silicon nitride, silica, silicon carbide or of any other material, even polymer, and the suspended structures are preferably made of silicon, silicon nitride or silicon carbide.

I. First Example of Manufacturing Method (FIGS. 5A to 5J)

Figure 5A:
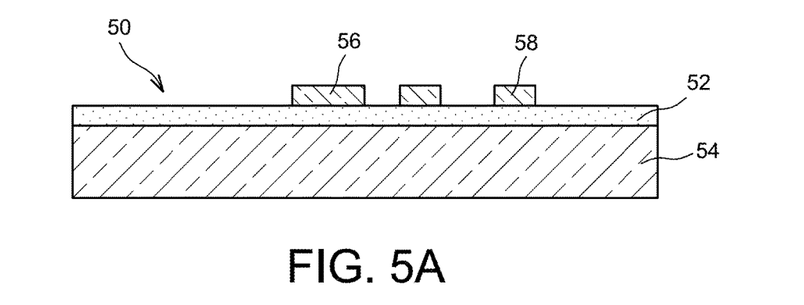

I.1 Manufacture of the Photonic Wafer (FIG. 5A)

The starting point in the manufacture of the device is a buried oxide (BOX) plate 50 comprising a layer of silica 52 of thickness 200 nm on a silicon substrate 54. It is structured so as to obtain the desired photonic circuits (standard process). Each waveguide 56 is made of silicon and has a cross-section of the order of, for example, 100×100 nm² to 500×500 nm². Each ring-shaped optical resonator 58 has an internal radius of the order of from 5 µm to 20 µm, a width of the order of 200 to 500 nm and a thickness of the order of 200 nm to 500 nm. The typical lengths of the intra-chip waveguides go from 100 µm to a few millimeters.

On this matter, reference should be made, for example, to the following documents:

US 2012/0063717, Method of producing a photonic device and corresponding photonic device, invention by Laurent Grenouillet et al.

US 2010/0265504, Optical device with superimposed photonic circuits for coupling to one or more optical waveguides, invention by Christophe Kopp et al.

Figure 5B:
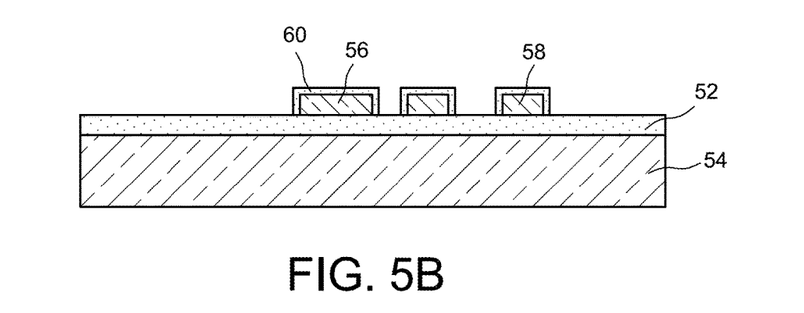
Figure 5C:
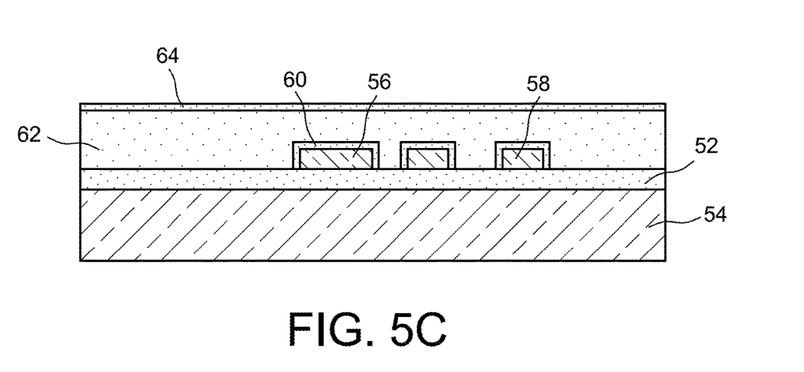

I.2 Preparation/Protection of the Wafer (FIGS. 5B and 5C)

A fine layer of oxide 60 is deposited to protect the optical waveguides made of silicon, for example using PECVD. This layer 60 has a thickness of, for example, 10 nm.

Then a sacrificial layer 62 of polysilicon is deposited with a depth of over 500 nm. This depth is, for example, 550 nm in order to leave, on the final release, a 50 nm space between the MEMS or NEMS used and the waveguide. (Alternatively, an etch stop layer of $HfO_2$ can be deposited directly onto the guides, or onto the few nanometers of previously deposited silicon oxide, then a deposit of for example 500 nm of silicon oxide made, which will act as a sacrificial layer for release using hydrofluoric acid).

Then a final thin oxide layer 64 of thickness 10 nm is deposited using PECVD. (This step is not applicable to the above mentioned alternative).

The surface of the structure 66 thus obtained is levelled and cleaned to prepare it for bonding. The layer 64 acts as a stop layer during the structuring of the MEMS or of the NEMS.

Figure 5D:
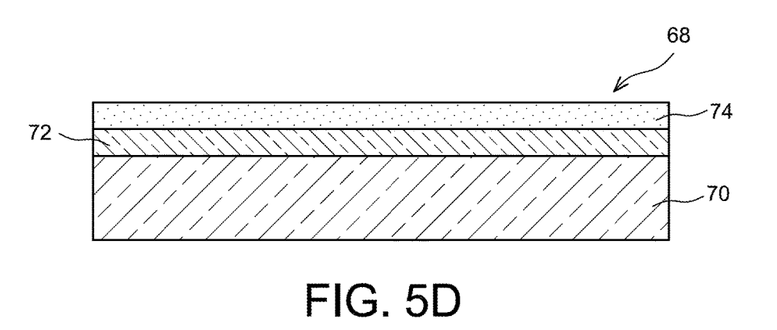
Figure 5E:
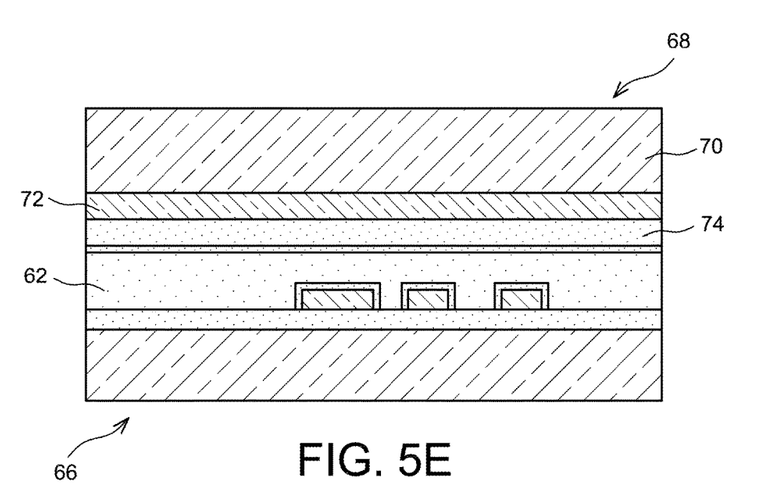
Figure 5F:
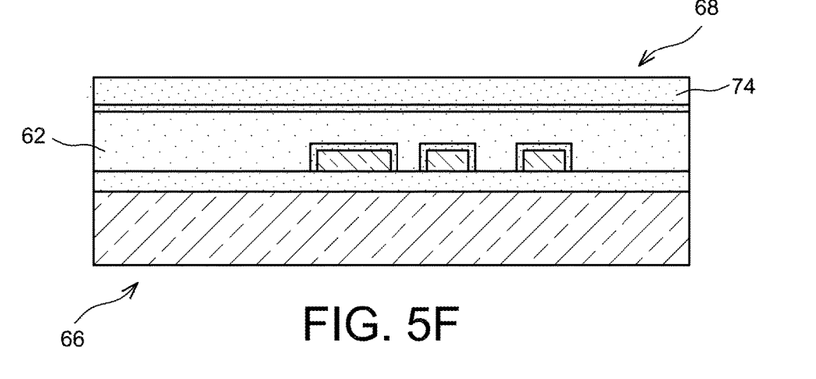

I.3 Bonding of the Upper Layer, Future MEMS or NEMS Layer (FIGS. 5D to 5F).

An SOI type wafer 68, comprising 500 µm of base Si 70, 400 nm of buried oxide BOX 72 and 200 nm of top silicon 74 is bonded to the surface of the photonic wafer formed by the structure 66. Bonding of the wafers 66 and 68 is achieved for example by molecular bonding. It should be pointed out that instead of an SOI type wafer, a Si wafer can be used which is thinned down and then levelled until the desired thickness is obtained.

The resulting structure is then thinned down by removing the entire thickness of silicon 70, that is, 500 μm, ending up on the buried oxide (BOX).

Then the buried oxide 72 is removed (FIG. 5F) and the top silicon 74 is levelled to obtain a desired thickness of the order of from 200 nm to 10 nm. Thus a stack of two wafers is obtained with a silicon/oxide interface. Thus before structuring of the NEMS or MEMS the configuration of an SOI is thus regained: 200 nm of top Si/10 nm of oxide /550 nm of polysilicon.

Figure 5G:
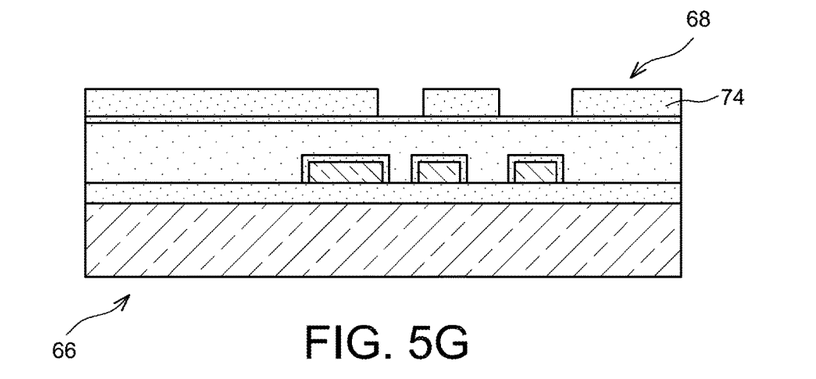
Figure 5H:
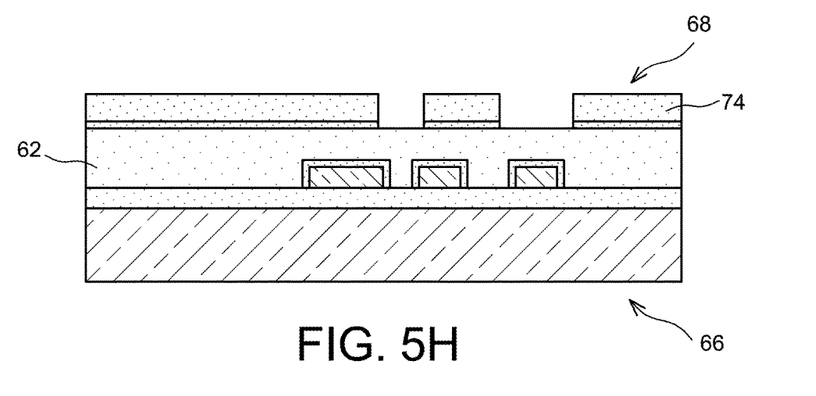
Figure 5I:
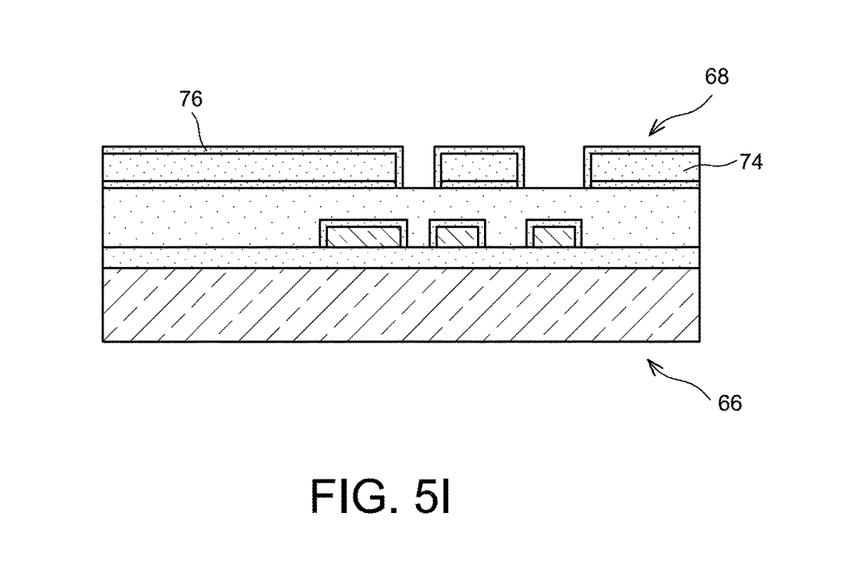

I.4 Structuring of MEMS or of NEMS arrays (FIGS. 5G to 5I)

Conventional reactive-ion etching (RIE) lithography/etching steps are carried out to structure the MEMS or NEMS in the silicon layer 74 (see for example the article by E. Mile et al. cited above). This then ends up on the 10 nm-thick oxide layer 62. (In the alternative mentioned above, however, this ends up directly on the 550 nm of silicon oxide which acts as the sacrificial layer).

Then (FIG. 5I) the MEMS or the NEMS are accordingly oxidised over a thickness of 10 nm for example, in order to protect these NEMS or MEMS structures during the release of the sacrificial layer made of Si. The resulting oxide layer has reference 76. (In the alternative mentioned above this step is not necessary).

The MEMS or NEMS array will have a smaller surface area than the photonic circuit in order to leave room for the introduction of light by means of optical fibres.

Then lithography, followed by etching of the oxide (10 nm+10 nm) is carried out using RIE (anisotropic etching) on the areas which have to be released. (In the alternative mentioned above this step is not necessary).

Figure 5J:
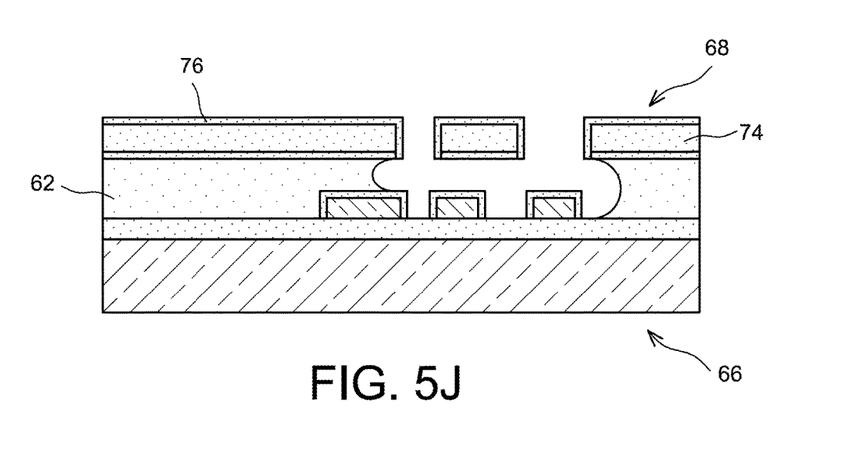

I.5 Release of the Moving Structures (FIG. 5J)

The MEMS or NEMS structures are released by isotropic etching of the polycrystalline silicon using XeF2. (In the alternative mentioned above another method is used: release is carried out using hydrofluoric acid, by etching the 550 nm of silicon oxide and by stopping on the $HfO_2$.

Finally, suspended MEMS or NEMS structures are obtained, made of 10 nm of oxide/200 nm to 50 nm of Si/20 nm of oxide, above silicon waveguides, coated with a layer of oxide whose thickness is between 5 nm and 10 nm and which is, for example, equal to 10 nm.

II. Second Example of Manufacturing Method (FIGS. 6A to 6E)

The difference between this second example and the first is due to the bonding of the MEMS or NEMS wafer onto the photonic wafer whilst retaining the profile (bonding on cavities).

Figure 6A:
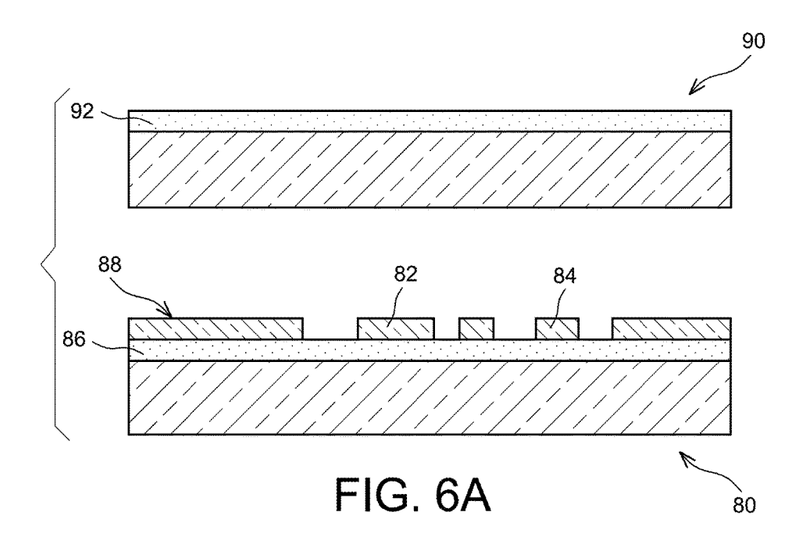

The photonic circuit remains the same. For the design of the latter, however, large bonding surfaces may advantageously be provided. One wafer is bonded directly onto the other, for example by molecular bonding. The wafers supporting the future MEMS or NEMS are made of silicon and are covered with an oxide which will make up both the bonding interface and the sacrificial layer.

FIG. 6A shows the wafer 80 carrying a waveguide 82 and an optical ring 84. These rest on the layer of silica 86 that the wafer 80 comprises. The bonding surface 88 provided for bonding of the wafers can also be seen.

The wafer 90 made of silicon can also be seen. It has a surface layer of silica 92 which is obtained by PECVD and has a thickness of the order of, for example, 10 nm to 500 nm. This layer 92 will act as a sacrificial layer, setting the interval between the optical resonator and the MEMS or NEMS structure.

Figure 6B:
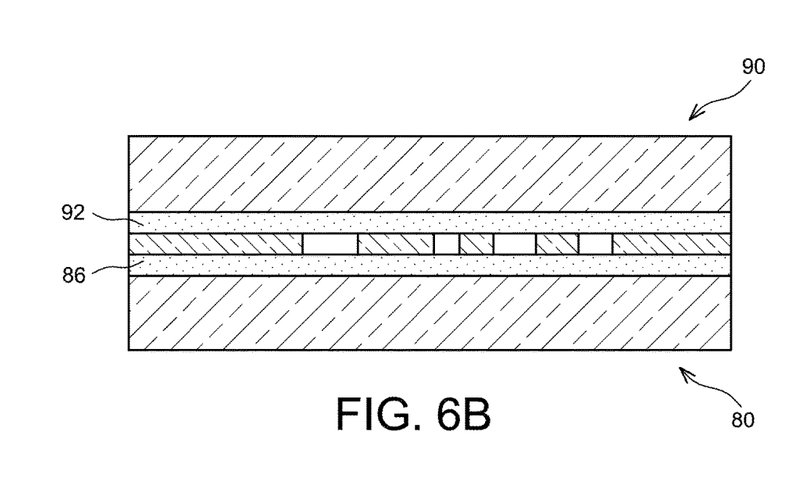
Figure 6C:
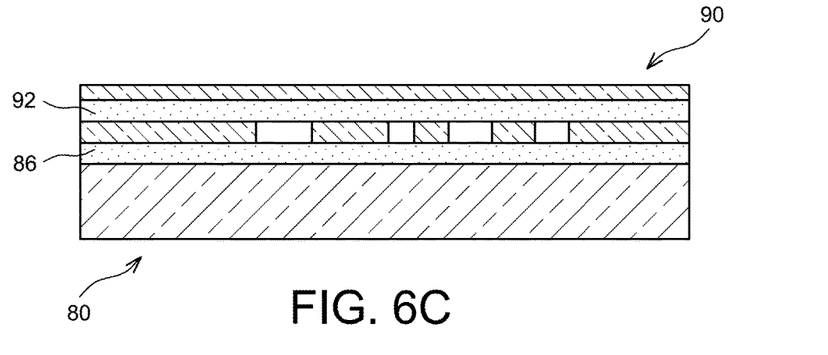

FIG. 6B shows the wafers 80 and 90 bonded to each other. The layer 92 of the wafer 90 is bonded to the surface of the wafer 80, whose reference is 88 in FIG. 6A.

Then (FIG. 6C), the wafer 90 is thinned out by physico-chemical grinding, then final levelling off (polishing) is carried out to achieve the desired thickness, of between 10 nm and 200 nm.

Figure 6D:
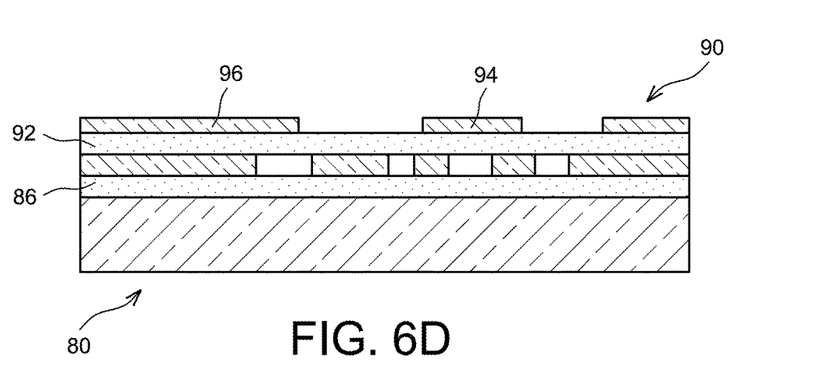
Figure 6E:
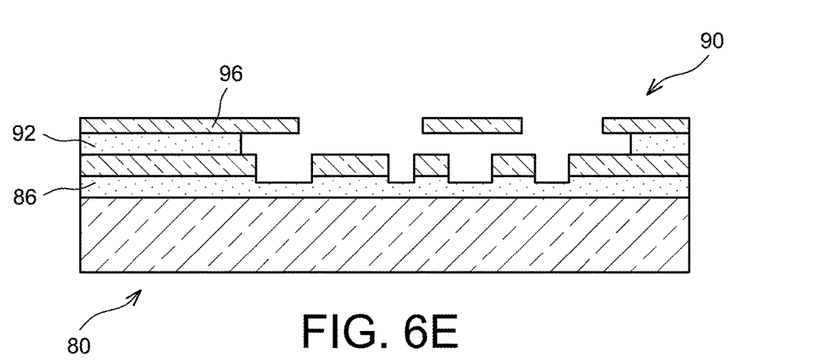

The MEMS or NEMS are then structured by lithography/etching (FIG. 6D). Reference 94 corresponds to these MEMS or these NEMS and reference 96 to their mechanical support.

All that is then needed (FIG. 6E) is to carry out release by, for example, HF vapour etching. In the example presented, the oxide which is found beneath the photonic circuit will undergo some etching during the release. This may be controlled in different ways: the oxide in the sacrificial layer is less dense than the thermal oxide which is placed beneath the photonic circuit and is therefore etched faster than the latter. It is also possible to carry out prior anisotropic etching of the silicon oxide in order to limit the HF isotropic etching time.

III. Third Example of Manufacturing Method

From the manufacturing method point of view, both standard "photonic circuit on silicon" and "MEMS or NEMS on silicon" methods may be combined:

The base wafer may be an SOI wafer comprising, for example, a top layer of thickness 220 nm and a BOX layer of thickness 2 μm.

A first lithography/etching cycle allows the waveguides and the optical resonators to be modelled in the top layer of the SOI wafer, as well as the coupling arrays, required for the connection with the optical fibres designed to link the optomechanical device to a laser and to means of photodetection.

Deposition of $SiO_2$, for example with a thickness of 500 nm, is then carried out.

Then levelling using chemical-mechanical polishing (CMP) is performed, with a stop of this CMP to define the vertical optical interval between the optical resonators and the mechanical resonators.

Then a stop layer is deposited, for example a layer of $HfO_2$ with a thickness of 20 nm, to ensure that release of the mechanical structure does not result in release of the optical guides and the optical resonators.

A lithography/etching cycle is carried out to open the stop layer/oxide stack and to model the anchorages of the future mechanical structures.

The layer of material wherein it is wished to form the mechanical structures is deposited. This is, for example, a layer of polycrystalline silicon with a thickness of 100 nm.

A lithography/etching cycle of the previous layer is performed to define the mechanical resonators.

Then the mechanical structures are released, for example using Hf vapour etching.

The optomechanical devices according to the invention, described with reference to FIGS. 3A, 3B and 4A, 4B comprise mechanical elements which make up the resonators. The invention is not limited to such an instance however: an optomechanical device which is in accordance with the invention can use one or more non-resonant mechanical elements, for example in order to detect a force such as a cellular force. In this case the optomechanical device uses no device for actuating the mechanical element or elements, only a device for detecting displacement of the element or elements, using an optical wave, as has been seen above.

In addition, particularly making reference to FIGS. 3B and 4B, it should be stated that the mechanical element of a device according to the invention may have either an element perpendicular to the plane of the layers from which the device is made, this element having an end anchored to the support that the device has, and an end capable of moving in a plane parallel to the plane of the layers, or an element parallel to the plane of the layers, suspended to the support via at least to ends, and able to move perpendicular to the plane of the layers.

The invention claimed is:

1. An optomechanical device comprising:
a support, and on the support:
at least one mechanical element which is anchored to the support and includes a portion which is designed to move relative to the support, and
a device for actuating the portion of the mechanical element and/or for detecting movement of the portion of mechanical element or frequency variations of said movement, wherein the actuation and/or detection device comprises an optical device:
which is fixed with respect to the support,
which comprises at least one optical wave guide and an optical resonator which is optically coupled to the at least one optical wave guide, wherein both the at least one optical wave guide and the optical resonator are fixed with respect to the support,
which is arranged beneath all or part of the portion of the mechanical element, between the portion of the mechanical element and the support, at a determined distance from the portion of the mechanical element,
and which is designed to propagate at least one optical wave which has a given wavelength, said optical wave being designed to interact with the mechanical element and cause movement of the portion of the mechanical element and/or be modified by movement of the portion of the mechanical element, and
wherein the optical device is at a determined distance from the mechanical element so that an evanescent field of the optical device interacts with the mechanical element,
wherein the mechanical element comprises a receiving zone, designed to receive one or more particles which can cause or modify movement of the mechanical element for the purposes of determining a physical property of the particle or of the particles from a signal supplied by the actuation and/or detection device.

2. Optomechanical device according to claim 1, wherein the mechanical element has either an element perpendicular to a plane of the layers from which the device is made, having an end anchored to the support and an end able to move in a plane parallel to the plane of the layers, or an element parallel to the plane of the layers, suspended to the support via at least two ends and able to move perpendicular to the plane of the layers.

3. Optomechanical device according to claim 1, wherein said mechanical element forms a mechanical resonator with a given resonance frequency.

4. Optomechanical device according to claim 3, comprising one optical device per mechanical element or one optical device for a group of mechanical elements with resonance frequencies which differ from each other.

5. Optomechanical device according to claim 1, wherein the number of optical devices is less than or equal to the number of mechanical elements.

6. An optomechanical device according to claim 1, wherein the optical resonator is in the form of a ring.

7. Optomechanical device according to claim 1, wherein the mechanical element comprises a substantially rectilinear beam, which has a first end anchored to the support, and a second end provided with a plate which forms the receiving zone.

8. Optomechanical device according to claim 7, wherein the beam is substantially perpendicular to the support and the plate is substantially perpendicular to the beam.

9. Optomechanical device according to claim 1, wherein the mechanical element forms a mechanical resonator whose resonance frequency varies when the receiving zone receives the particle or particles.

10. Optomechanical device according to claim 1 wherein the receiving zone is designed to receive material particles.

11. Optomechanical device according to claim 1, wherein the receiving zone comprises a material designed to absorb particles formed by photons in a predefined range of electromagnetic frequencies.

12. Optomechanical device according to claim 1, wherein the optical waveguide is at a determined distance from the mechanical element so that the evanescent field of the optical waveguide interacts with the mechanical element.

13. An optomechanical device comprising:
a support, and on the support:
at least one mechanical element which is anchored to the support and includes a portion which is designed to move relative to the support, and
a device for actuating the portion of the mechanical element and for detecting movement of the portion of mechanical element or frequency variations of said movement, wherein the actuation and detection device comprises an optical device:
which is fixed with respect to the support,
which comprises at least one optical wave guide, which is arranged beneath all or part of the portion of the mechanical element between the portion of the mechanical element and the support, at a determined distance from the portion of the mechanical element,
and which is designed to propagate at least one optical wave which has a given wavelength, said optical wave being designed to interact with the mechanical element and cause movement of the portion of the mechanical element and the optical wave being modified by movement of the portion of the mechanical element, and
wherein the optical device is at a determined distance from the mechanical element so that an evanescent field of the optical device interacts with the mechanical element,
wherein the mechanical element comprises a receiving zone, designed to receive one or more particles which can cause or modify movement of the mechanical element for the purposes of determining a physical property of the particle or of the particles from a signal supplied by the actuation and/or detection device.

14. The optomechanical device according to claim 13, wherein the optical device further comprises an optical resonator which is optically coupled to the at least one optical wave guide wherein both the at least one optical wave guide and the optical resonator are fixed with respect to the support.

* * * * *